United States Patent
Ikemoto et al.

(10) Patent No.: US 10,899,994 B2
(45) Date of Patent: Jan. 26, 2021

(54) METHOD FOR PRODUCING POLYUNSATURATED FATTY ACID-CONTAINING COMPOSITION

(71) Applicant: NISSHIN PHARMA INC., Chiyoda-ku (JP)

(72) Inventors: Hiroyuki Ikemoto, Fujimino (JP); Kenji Takemoto, Fujimino (JP); Masataka Harata, Ueda (JP); Shingo Nonaka, Ueda (JP); Hideki Kanai, Ueda (JP)

(73) Assignee: NISSHIN PHARMA INC., Chiyoda-ku (JP)

( * ) Notice: Subject to any disclaimer, the term of this patent is extended or adjusted under 35 U.S.C. 154(b) by 0 days.

(21) Appl. No.: 16/621,464

(22) PCT Filed: Jun. 14, 2018

(86) PCT No.: PCT/JP2018/022654
§ 371 (c)(1),
(2) Date: Dec. 11, 2019

(87) PCT Pub. No.: WO2018/230622
PCT Pub. Date: Dec. 20, 2018

(65) Prior Publication Data
US 2020/0172829 A1    Jun. 4, 2020

(30) Foreign Application Priority Data
Jun. 14, 2017 (JP) ................................. 2017-116356

(51) Int. Cl.
C11B 7/00 (2006.01)
(52) U.S. Cl.
CPC .......... C11B 7/0025 (2013.01); C11B 7/0016 (2013.01); C11B 7/0083 (2013.01)
(58) Field of Classification Search
None
See application file for complete search history.

(56) References Cited

U.S. PATENT DOCUMENTS

| | | | | |
|---|---|---|---|---|
| 2,838,553 | A * | 6/1958 | Ayres | C11B 3/06 554/195 |
| 5,189,189 | A * | 2/1993 | Misawa | C07C 67/60 554/194 |
| 8,173,826 | B2 * | 5/2012 | Prakash | C11B 7/0083 554/206 |
| 8,680,305 | B2 * | 3/2014 | Sakaguchi | C07C 67/58 554/175 |
| 9,365,800 | B2 * | 6/2016 | Harata | C11C 1/007 |
| 10,189,770 | B2 * | 1/2019 | Mankura | B01D 15/00 |
| 10,196,584 | B2 * | 2/2019 | Tabata | C07C 67/58 |
| 10,597,607 | B2 * | 3/2020 | Harata | C11C 1/08 |
| 2010/0324318 | A1 * | 12/2010 | Prakash | C11C 3/003 554/206 |
| 2011/0224452 | A1 | 9/2011 | Sakaguchi et al. | |
| 2013/0317241 | A1 * | 11/2013 | Breivik | C07C 51/48 554/194 |
| 2015/0252288 | A1 | 9/2015 | Harata et al. | |
| 2018/0074527 | A1 | 3/2018 | Kuemmerling et al. | |
| 2018/0155268 | A1 | 6/2018 | Mankura et al. | |
| 2019/0144780 | A1 * | 5/2019 | Harata | C11B 7/00 554/176 |

FOREIGN PATENT DOCUMENTS

| | | | |
|---|---|---|---|
| CN | 205517304 U | * | 8/2016 |
| JP | 4-159398 A | | 6/1992 |
| JP | 2786748 B2 | | 8/1998 |
| JP | 2895258 B2 | | 5/1999 |
| JP | 2935555 B2 | | 8/1999 |
| JP | 3001954 B2 | | 1/2000 |
| JP | 2010-64974 A | | 3/2010 |
| JP | 2013-542927 A | | 11/2013 |
| JP | 2015-91940 A | | 5/2015 |
| JP | 2015091940 A | * | 5/2015 |
| JP | 2018-515728 A | | 6/2018 |
| WO | WO 2014/054435 A1 | | 5/2014 |
| WO | WO 2016/194360 A1 | | 12/2016 |
| WO | WO 2017/191821 A1 | | 11/2017 |

OTHER PUBLICATIONS

English-Language Machine Translation CN 205517304 (2016) (Year: 2016).*
English-Language Machine Translation JP 2015091940 (2015) (Year: 2015).*
Yuri, T. et al, "Establishment of Method for Industrially Producing High Purity DHA Ester (Study of Separation and Recovery of DHA Ethyl Ester and Solvents, etc. by Silver Nitrate Method," DHA Highly Refined Extraction Technology Development Business Research Report, 1995-1996, pp. 103-111, (16 total pages With Partial English Translation).
International Search Report dated Aug. 28, 2018 in PCT/JP2018/022654 filed on Jun. 14, 2018, 2 pages.

* cited by examiner

*Primary Examiner* — Alexander R Pagano
(74) *Attorney, Agent, or Firm* — Oblon, McClelland, Maier & Neustadt, L.L.P.

(57) ABSTRACT

Provided is a method for producing a polyunsaturated fatty acid while suppressing deterioration of a silver salt solution. A method for producing a polyunsaturated fatty acid-containing composition, the method comprising: supplying a raw material solution comprising an alkyl ester of polyunsaturated fatty acid and an aqueous solution comprising a silver salt to a flow channel mixer to contact the raw material solution with the aqueous solution; and collecting the aqueous solution comprising the silver salt which has been contacted with the raw material solution, in which the supplying the aqueous solution comprising the silver salt to the flow channel mixer and the collecting the same are performed concurrently.

24 Claims, 3 Drawing Sheets

METHOD FOR PRODUCING POLYUNSATURATED FATTY ACID-CONTAINING COMPOSITION

TECHNICAL FIELD

The present invention relates to a method for producing a polyunsaturated fatty acid-containing composition, and suppression of deterioration of a silver salt solution to be used in the producing method.

BACKGROUND ART

A polyunsaturated fatty acid (PUFA), such as eicosapentaenoic acid (EPA), docosahexaenoic acid (DHA) and docosapentaenoic acid (DPA), has been revealed for pharmacological effects thereof recently, and has been used as a raw material for drugs and health foods. Production of a PUFA by chemical synthesis is not easy. Therefore, almost all of PUFAs utilized industrially have been currently produced by extraction or purification from marine organisms-derived PUFA-rich raw materials, e.g., fish oils. However, a biological raw material is a mixture of many types of fatty acids which are different in the number of carbon atoms, the number or position of double bonds, the component ratio of stereoisomers and the like from each other, and therefore a content of a PUFA in the raw material is not always high. For these reasons, it has been demanded to selectively purify a desired PUFA from a biological raw material.

In Patent Literatures 1 to 7, a method is disclosed, in which a raw material containing a PUFA and an aqueous solution containing a silver salt are brought into contact with each other to produce a complex of the PUFA and silver, then the complex is eluted into an aqueous phase, and then the PUFA is extracted from the aqueous phase with an organic solvent. In the method disclosed in Patent Literatures1 to 7, a PUFA-containing raw material is supplied to a large amount of an aqueous silver salt solution and the resultant solution is preferably stirred to increase the chance of contact between the aqueous solution with the PUFA-containing raw material and therefore promote production of a complex of the PUFA and silver. However, in the above-mentioned conventional method, it is required to use a large-scale facility for producing a PUFA in a large amount, and a batch of an aqueous silver salt solution that has been contacted with a raw mate t be collected at very extraction of the PUFA. Therefore, the conventional method is inefficient from the industrial viewpoint. In addition, in the conventional method, there are many chances of contact of the aqueous silver salt solution with oxygen and therefore deterioration of the aqueous silver salt solution may be accelerated. Furthermore, the presence of peroxide contained in a raw material may also deteriorate the aqueous silver salt solution (Patent Literature 7). The deteriorated aqueous silver salt solution is regenerated into silver after collection, and is then re-processed into a silver salt. In this manner, the deteriorated aqueous silver salt solution can be re-used. However, the cost for reproduction of silver and the cost for processing into a silver salt are expensive, and therefore use of a large amount of an aqueous silver salt solution and deterioration of the aqueous silver salt solution may increase the cost of production of a PUFA.

CITATION LIST

Patent Literature

Patent Literature 1: JP 3001954 B2
Patent Literature 2: JP 2786748 B2
Patent Literature 3: JP 2935555 B2
Patent Literature 4: JP 2895258 B2
Patent Literature 5: JP 2015-091940 A
Patent Literature 6: WO 2014/054435 A
Patent Literature 7: WO 2016/194360 A

SUMMARY OF INVENTION

Technical Problem

The present invention relates to a provision of a method by which it becomes possible to produce a PUFA with higher efficiency and lower cost and it also becomes possible to prevent deterioration of a silver salt solution used for the production of a PUFA.

Solution to Problem

The inventors of the present invention have found, in production of a PUFS using a silver salt solution, a method in which production of a complex of a PUFA with silver and collection of an aqueous phase containing the complex are carried out continuously by concurrently performing supply of a silver salt solution to a reaction vessel using a flow channel mixer as the reaction vessel for contacting the silver salt solution and a raw material fat or oil, and collection of the silver salt solution which has been contacted with the raw material fat or oil. Furthermore, the inventors of the present invention have found that according to the method, it is possible to suppress deterioration of a silver salt solution in the process of producing a PUFA.

Accordingly, the present invention provides the following.

[1] A method for producing a polyunsaturated fatty acid-containing composition, the method comprising:

supplying a raw material solution comprising an alkyl ester of a polyunsaturated fatty acid and an aqueous solution comprising a silver salt to a flow channel mixer to contact the raw material solution with the aqueous solution; and collecting the aqueous solution comprising the silver salt which has been contacted with the raw material solution;

wherein the supply of the aqueous solution comprising the silver salt to the flow channel mixer and the collection of the same are performed concurrently.

[2] The method according to [1], further comprising:

supplying the aqueous solution comprising the silver salt which has been collected from the flow channel mixer and an organic solvent into an extraction vessel to contact the aqueous solution with the organic solvent; and collecting the organic solvent which has been contacted with the aqueous solution comprising the silver salt;

wherein the supply of the aqueous solution comprising the silver salt to the extraction vessel and the collection of the organic solvent are performed concurrently. [3] The method according to [1] or [2], wherein the collection of the aqueous solution comprising the silver salt which has been contacted with the raw material solution comprises collecting a mixed solution of the aqueous solution comprising the silver salt and the raw material solution from the flow channel mixer and then fractionating the aqueous solution comprising the silver salt from the collected, mixed solution.

[4] The method according to [2] or [3], wherein the collection of the organic solvent which has been contacted with the aqueous solution comprising the silver salt comprises collecting a mixed solution of the aqueous solution comprising the silver salt and the organic solvent from the extraction vessel and then fractionating the organic solvent from the collected mixed solution.

[5] The method according to any one of [1] to [4], further comprising: supplying the raw material solution collected from the flow channel mixer to the flow channel mixer again.

[6] The method according to any one of [1] to [5], wherein the supply of the aqueous solution comprising the silver salt to the flow channel mixer, the contact of the aqueous solution comprising the silver salt with the raw material solution, and the collection of the aqueous solution comprising the silver salt from the flow channel mixer are performed under hypoxic conditions.

[7] The method according to any one of [1] to [6], wherein a linear velocity of the aqueous solution comprising the silver salt in the flow channel mixer 5 cm/sec or more.

[8] The method according to any one of [1] to [7], wherein the flow channel mixer has an inner diameter of 0.1 to 100 cm and a length of 0.05 to 10 m.

[9] The method according to any one of [1] to [8], wherein a retention time of the aqueous solution comprising the silver salt in the flow channel mixer is from 0.02 to 300 seconds.

[10] The method according to any one of [1] to [9], wherein a temperature of the aqueous solution comprising the silver salt when being contacted with the raw material solution is from 5° C. to 30° C.

[11] The method according to any one of [2] to [10], wherein the extraction vessel is a flow channel mixer.

[12] The method according to [11], wherein a linear velocity of the aqueous solution comprising the silver salt in the extraction vessel is 0.5 cm/sec or more.

[13] The method according to [11] or [12], wherein the extraction. vessel has an inner diameter of 0.1 to 100 cm and a length of 0.05 to 10 m.

[14] The method according to any one of [11] to [13], wherein a retention time of the aqueous solution comprising the silver salt in the extraction vessel is from 0.02 to 300 seconds.

[15] The method according to any one of [2] to [14], wherein a temperature of the aqueous solution comprising the silver salt when being contacted with the organic solvent is from 30° C. to 80° C.

[16] The method according to any one of [1] to [15], wherein the raw material solution comprising an alkyl ester of a polyunsaturated fatty acid has such as oxidation index that a POV is 10 or less, or AV is 0.3 or less.

[17] The method according to any one of [1] to [16], wherein the polyunsaturated fatty acid comprises eicosapentaenoic acid or docosahexaenoic acid.

Advantageous Effects of Invention

In the method for producing a PUFA-containing composition according to the present invention, the contact of the raw material fat or oil and the silver salt solution and the collection of the silver salt solution after reaction with the raw material fat or oil are performed continuously and concurrently. In the method of the present invention, unlike the conventional method for producing PUFA by a batch mode, an operation of collecting the silver salt solution in every PUFA collection is unnecessary. Furthermore, according to the method of the present invention, the amount of the silver salt solution used can be reduced, and deterioration of the silver salt solution can be suppressed. Therefore, according to the present invention, both of reduction in size of the facility used in the PUFA production and reduction in cost can be achieved.

DESCRIPTION OF EMBODIMENTS

Figure 1:
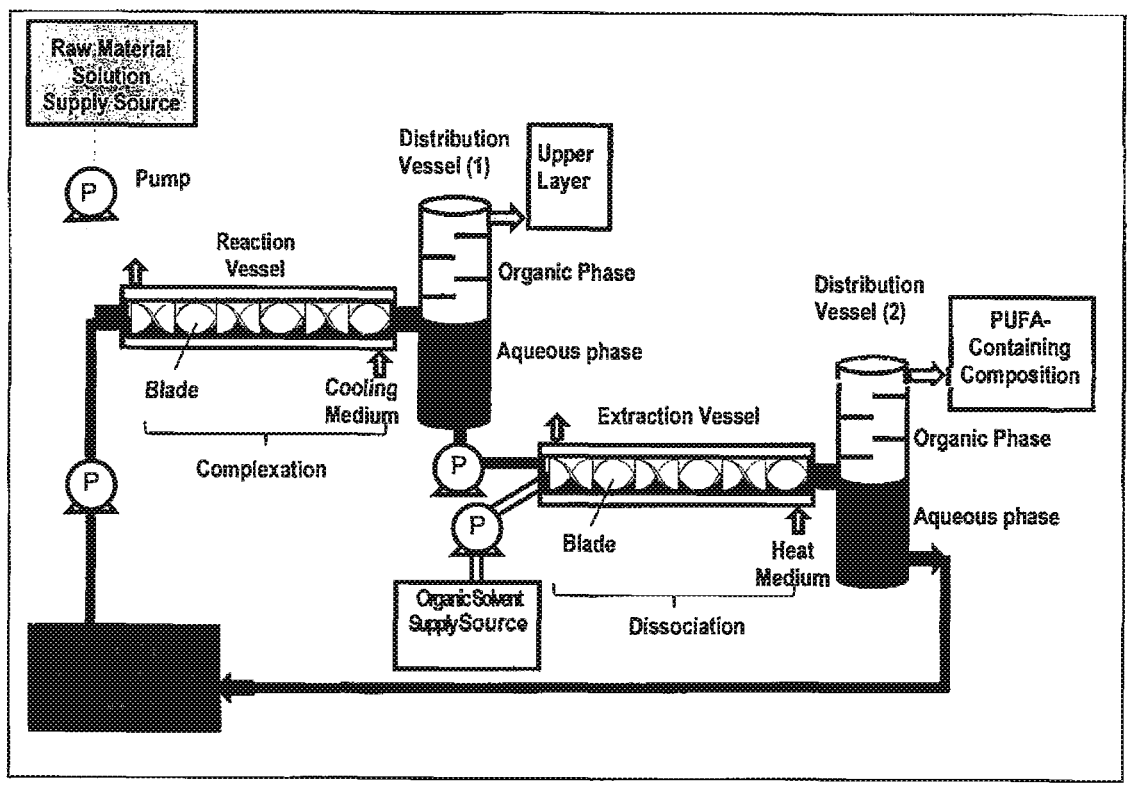
FIG. 1 illustrates a schematic diagram of an apparatus for producing a PUFA-containing composition using a flow channel mixer for a reaction vessel and an extraction vessel.

The method for producing a polyunsaturated fatty acid-containing composition of the present invention comprises supplying a raw material solution comprising an alkyl ester of a polyunsaturated fatty acid and an aqueous solution comprising a silver salt to a reaction vessel to contact the raw material solution with the aqueous solution; and collecting the aqueous solution comprising the silver salt which has been contacted with the raw material solution. In the method, the supply of the aqueous solution comprising the silver salt to the reaction vessel and the collection of the same are performed concurrently.

In the present specification, the term "polyunsaturated fatty acid (PUFA)" refers to a fatty acid having two or more unsaturated bonds. Examples of the PUFA include linoleic acid (LA, 18:2n-6), linolenic acid (GLA, 18:3n-6), arachidonic acid (AA, 20:4n-6), alpha-linolenic acid (ALA) 18:3n-3), eicosatetraenoic acid (ETA, 20:4n-3), docosapentaenoic acid (DPA, 22:5n-3), eicosapentaenoic acid (EPA, 20:5n-3), and docosahexaenoic acid (DHA, 2216n-3). In the method for producing the PUFA-containing composition of the present invention, the PUFA to be contained in the produced composition is preferably at least one selected from the group consisting of EPA, DHA, and DPA, more preferably at least one selected from the group consisting of EPA and DHA, and still more preferably EPA.

In the method of the present invention, a PUFA alkyl ester is separated and purified by utilizing the fact that the solubility of PUFA in a silver salt solution varies when a silver salt focus a complex at a double bond part in the PUFA. In the method of the present invention, alkyl esters of EPA, DHA, and DPA having 5 or more unsaturated bonds and fatty acid alkyl esters having 4 or less unsaturated bonds such as AA and ETA can be separated and purified with high efficiency.

A major example of the raw material for the PUFA-containing composition which can he used in the present invention is a natural product-derived oil or fat mixture which contains the above-mentioned PUFA. Specific examples of the raw material include: an oil or fat derived from a marine animal, for example, fish, or a plankton; and an oil or fat derived from a microorganism, e.g., an alga. Among these oils or fats, an oil or fat derived from a fish such as sardine and yellowtail and an oil or fat derived from an alga are preferred.

The raw material of the PUFA-containing composition to be used in the present invention is preferably an oil or fat containing a desired PUFA (preferably at least one selected from the group consisting of EPA, DHA, and DPA, more preferably at least one selected from the group consisting of EPA and DHA, and still more preferably EPA) in an amount of preferably 15% by mass or more, and more preferably 40% by mass or more relative to the total amount of fatty acid(s) contained. The raw material preferably contains an EPA, DHA, and DPA at a large total content as possible. From the viewpoints of cost and availability, the total content of EPA, DHA, and DPA in the raw material may be preferably 65% by mass or less, more preferably 60% by mass or less, and still more preferably 55% by mass or less in the total fatty acids contained. The PUFA in the raw material may be present in a form of a free fatty acid or in a form of fatty acid chain such as mono-, di-, or tri-glyceride.

In the method of the present invention, the PUFA in the raw material is alkyl-esterified. Preferably, the raw material contains an alkyl ester of a desired PUFA (preferably at least one selected from the group consisting of EPA, DNA, and DPA, more preferably at least one selected from the group consisting of EPA and DHA, and still more preferably EPA). An example of the alkyl group constituting the alkyl ester of the PUFA includes a linear or branched alkyl group having 1 to 6 carbon atoms, preferably a methyl group or an ethyl group, and more preferably an ethyl group. A higher degree of alkyl esterification is preferably, and preferably 800 or more, and more preferably 90% or more of the total amount of the desired PUFA (including a free form thereof) contained in the raw material may be alkyl-esterified.

The raw material containing the alkyl ester of the PUFA can be produced by subjecting an oil or fat containing he PUFA and an acid having a desired alkyl group to an esterification reaction by a well-known method. For example, an alkyl-esterified product of a PUFA can be easily obtained by subjecting an oil or fat containing triglyceride of the PUFA to a saponification treatment, a transesterification, or the like. Alternatively, a commercially available oil or fat may be used as a raw material containing the alkyl ester of the PUFA. For example, it is preferable to use a commercially available fish oil-derived fat or oil, and the like in which the type and amount of a PUFA contained are standardized.

From the viewpoint of quality preservation of the PUFA-containing composition produced in the present invention and prevention of deterioration of the aqueous solution containing a silver salt, it is preferred that the raw material containing the alkyl ester of the PUFA used in the present invention preferably has a small oxidation index. The oxidation index of lipids can be represented by, for example, peroxide value (POV) and acid value (AV). The raw material containing the alkyl ester of the PUFA used in the present invention has a POV (mEq/kg) of preferably 10 or less and more preferably 5 or less, or an AV (mg/g) of preferably 0.3 or less, and more preferably 0.2 or less. More preferably, the raw material containing the alkyl ester of the PUFA used in the present invention has a POV of 10 or less and an AV of 0.3 or less, and more preferably a POV of 5 or less and an AV of 0.2 or less. The POV can be measured by, for example, an iodine titration method (ISO 3960:2007). The AV can be measured by, for example, potassium hydroxide titration method (ISO 660: 2009).

(1. Method for Producing PUFA-Containing Composition)
(1-1. Production of Complex)

In the method for producing the PUFA-containing composition of the present invention, the raw material containing the alkyl ester of the PUFA described above is, in a form of a liquid (a raw material solution), contacted with the aqueous solution containing a silver salt (also referred to as a "silver salt solution" in the present specification). For the purpose of keeping the liquid state at a temperature upon contact with the silver salt solution, the raw material may be dissolved in or diluted with an organic solvent or another oil, as needed. Examples of the organic solvent include ethyl acetate, chloroform, carbon tetrachloride, diethyl ether, hexane, and cyclohexane.

The silver salt contained in the silver salt solution used in the method of the present invention is not particularly limited as long as the silver salt can form a complex with the unsaturated bond in a PUFA, and examples of the silver salt include silver nitrate, silver perchlorate, silver tetrafluoroborate, and silver acetate. Among these, silver nitrate is preferable. A solvent for the silver salt solution may be water or a solvent mixture of water and a compound having a hydroxyl group such as glycerin or ethylene glycol. Water is preferably used. The concentration of the silver salt in the silver salt solution may be 20% by mass or more, and preferably 30% by mass or more. In a preferred. embodiment, the concentration of the silver salt in the silver salt solution is from 20% to 80% by mass, and preferably from 30% to 70% by mass When the raw material solution is contacted with the silver salt solution, a complex of the PUFA and silver (also referred to as a "PUFA-silver complex" in the present specification) is formed. The complex formed moves into an aqueous phase, that is, a phase of the silver salt solution. Therefore, a solution containing the PUFA-silver complex can be obtained by collecting the silver salt solution which has been contacted with the raw material solution.

In the method of the present invention, a flow channel mixer is used as a reaction vessel used for contacting the raw material solution with the silver salt solution The flow channel mixer is an apparatus having a flow channel having an inlet port and a discharge port for a liquid material, which enables mixing or stirring of two or more different liquid materials in the flow channel. The flow channel mixer may be of a type in which different liquid materials to be mixed pass in the same direction in the flow channel (for example, a concurrent-flow-mode), or may be of a type in which different liquid materials to be mixed pass in the reverse direction in the flow channel (for example, a countercurrent-flow-mode). Any appropriate type of mixer may be selected appropriately in consideration of, for example, the flowability of the liquid material, the specific gravity, ease of separation of the liquid materials, the specific gravity difference. A concurrent-flow-mode flow channel mixer is preferable because it has excellent stirring efficiency, and thus mixing can be performed in a short time and the contact time between the liquid materials can be relatively shortened. As a mechanism for mixing or stirring the liquid materials provided in the flow channel mixer, a movable stirrer such as a propeller installed in the flow channel, a blade, or an orifice (stirring is performed using the resistance of the liquid against these components) provided in the flow channel are exemplified, and one or a combination of two or more thereof can be used.

Preferred examples of the embodiment of the flow channel mixer that can be used in the present invention include a static fluid mixer (for example, a static mixer or an in-line mixer, which has a blade, a fin, and the like provided therein for mixing fluid), a press-fit-type mixer (for example, an in-line mixer equipped with a venturi orifice), an element-laminated mixer (for example, an in-line mixer having a laminate with many through-holes for mixing mixing), and a homomixer (for example, an in-line mixer with a stator, a turbine rotating at high speed, or the like). Specific examples of the static fluid mixer include a static mixer (Models; for example, T-3, T-4, N10, and N60, Noritake Co, Ltd.), an in-line mixer (Model: TD, Hokuto MfG, Co, Ltd.), an OHR mixer (Model: MX10, OHR Laboratory Corporation). Specific example of the press-in type mixer include a VR line mixer (for example, VRX10 and VRX20; Nagoya Oshima Machinery Co.,Ltd.). Specific examples of the element-laminated mixer include a MSE static mixer (ISEL Co, Ltd.). Specific examples of the homomixer include (Pipeline Homomixer; PRIMIX Corporation). However, examples of the flow channel mixer that can be used in the present invention are not limited to these.

In the method of the present invention, it is enough that the raw material solution containing the alkyl ester of the PUFA can be contacted with the silver salt solution in the reaction vessel. For example, the raw material solution and the silver salt solution may be separately supplied to the reaction vessel to be contacted with each other in the reaction vessel, or the raw material solution and the silver salt solution mixed beforehand may be supplied to the reaction vessel to be contacted with each other in the reaction vessel.

The temperature of the silver salt solution upon contact with the raw material solution is preferably from 5° C. to 30° C., and more preferably 15° C. to 30° C. Examples of a method for maintaining the temperature of the silver salt solution upon contact with the raw material solution within the above range, include a method in which the raw material solution and/or the silver salt solution is warmed or cooled to a temperature falling within the above range and then the raw material solution and the silver salt solution are contacted with each other, a method in which the temperature of the reaction vessel for contact of the raw material solution with the silver salt solution is kept within the above range, and a combination of these methods.

In the method of the present invention, the supply of the silver salt solution to the reaction vessel and the collection of the silver salt solution containing the complex, which has been contacted with the raw material solution in the reaction vessel, are performed concurrently with one another. Therefore, in the method of the present invention, unlike the conventional batch-mode methods, it is not necessary to replace the whole of the silver salt solution in the reaction vessel by fresh one after the complex producing reaction, and the collection of the silver salt solution containing the complex can be continued while continuing the supply of the silver salt solution to the reaction vessel and the contact between the silver salt solution and the raw material solution. Therefore, in the method of the present invention, the contact between the raw material solution and the silver salt solution and the collection of the silver salt solution containing the complex are performed continuously (that is, in a continuous mode).

In the method of the present invention, the raw material solution containing the alkyl ester of the PUFA can be supplied to the reaction vessel continuously or intermittently. Preferably, in the method of the present invention, the supply of the raw material solution to the reaction vessel and the collection of the raw material solution which has been contacted with the silver salt solution are performed concurrently with each other. More preferably, a process of supplying and collecting the raw material solution is performed continuously (that is, in a continuous mode) and concurrently with a process of supplying and collecting the silver salt solution.

The supply of the silver salt solution and the raw material solution into the reaction vessel is preferably performed via a flow channel (hereinafter, referred to as a "supply channel") that is fluid-communicated with the reaction vessel. The supply channels are separately provided for supplying the silver salt solution and for supplying the raw material solution, and establish fluid communication of supply sources for the silver salt solution and the raw material solution with the reaction vessel, respectively. Each of the supply channels may be provided with, for example, a valve, a pump, and a vacuum tube. Each of the supply channels may be directly connected to the reaction vessel or the supply channels may be connected to each other collectively and then connected to the reaction vessel. The inner diameter of the reaction vessel is referably from 0.1 to 100 cm, and more preferably from 0.3 to 43 cm. The length of the reaction vessel is preferably from 0.05 to 10m, and more preferably from 0.1 to 4m. The retention time of the silver salt solution in the reaction vessel is preferably about from 0.02 to 300 seconds, and more preferably about from 0.04 to 150 seconds. More preferably, the retention time of the silver salt solution and the raw material solution in the reaction vessel is about from 0.02 to 300 seconds, and more preferably about from 0.04 to 150 seconds.

In the method of the present invention, the linear velocity of the silver salt solution in the reaction vessel is preferably 0.5 cm/sec or more, and more preferably from 0.5 to 400 cm/sec. More preferably, the linear velocity of the raw material solution and the silver salt solution in the reaction vessel is 0.5 cm/sec or more, and more preferably from 0.5 to 400 cm/sec. When the linear velocity of the silver salt solution is low, the efficiency of complex production may be reduced and the yield of the desired PUFA may be reduced. On the other hand, when the linear velocity of the silver salt solution and the raw material solution is high, there is a possibility that the seperation may fail in a distribution vessel, and the intelnal pressure of the reaction vessel is increased, thereby increasing a risk of damage.

In the present specification, the linear velocity of the liquid (for example, a raw material solution, a silver salt solution, or an organic solvent) in the reaction vessel or extraction vessel means a value calculated from the length of the reaction vessel or extraction vessel and time required for the liquid to pass through the reaction vessel or the extraction vessel (that is, the retention time of the liquid in the vessel), [length of reaction vessel or extraction vessel/time required for liquid to pass through reaction vessel or extraction vessel]. Here, [time required for liquid to pass through reaction vessel or extraction vessel] (the retention time of the liquid in the vessel) means a value obtained by dividing [volume of liquid in reaction vessel or extraction vessel] by [flow velocity of liquid in reaction vessel or extraction vessel]. In a case where a plurality kinds of liquids are present in the reaction vessel or the extraction vessel, the [volume of liquid in reaction vessel or extraction vessel] for one kind of liquid is [proportion of the liquid in total volume of liquids]×[volume of reaction vessel or extraction vessel]. For example, in a case where the liquids flowing in the reaction vessel are the raw material solution, the silver salt solution, and the organic solvent, [time required for silver salt solution to pass through reaction vessel] is a value obtained by dividing [volume of reaction vessel×{volume of silver salt solution/(total volume of raw material solution, silver salt solution, and organic solvent)}] by [flow velocity of the sliver salt solution in reaction vessel]. The linear velocity of a liquid in the reaction vessel or the extraction vessel can be appropriately adjusted by controlling the size of the reaction vessel or the extraction vessel, or the flow velocity of the liquid.

The silver salt solution and the raw material solution supplied to the reaction vessel are stirred together in the reaction vessel and contacted with each other. This contact produces a PUFA-silver complex in the silver salt solution.

In the method of the present invention, the mixed solution of the silver salt solution containing the produced PUFA-silver complex and the raw material solution is collected together from the reaction vessel Next, the silver salt solution is fractionated from the collected mixed solution. Preferably, the liquid containing the raw material solution and the silver salt solution that has flowed out of the reaction vessel is transferred to distribution vessel (1) (a distribution vessel for distributing the silver salt solution and the raw material solution) which is fluid-communicated with the reaction vessel, and the liquid is distributed to a phase of the raw material solution (organic phase) and a phase of the silver salt solution (aqueous phase) due to the specific gravity difference. When the distributed aqueous phase is fractionated, it is possible to collect the silver salt solution containing the complex. Furthermore, when the distributed organic phase is fractionated, it is possible to collect the used raw material solution. Collection of the silver salt solution and the raw material solution from the distribution vessel (1) can be performed through the flow channel for collection of each connected to the distribution vessel (1) (hereinafter, referred to as a collection channel in the present specification). In order to collect the distributed organic phase and aqueous phase easily, preferably, an outlet port of the silver salt solution from the distribution vessel (1) is arranged on the bottom surface or lower wall surface of the distribution vessel (1), and an outlet port of the raw material solution is arranged on the top surface or upper wall surface of the distribution vessel (1). Also, preferably, the silver salt solution may be suctioned through a nozzle arranged at a lower part, preferably on the bottom surface, of the distribution vessel (1) to be collected from the distribution vessel (1). The outlet ports and nozzles for the silver salt solution and the raw material solution in the distribution vessel (1) are connected to the respective collection channels. The collection channel may be provided with, for example, a valve, a pump, and a valve.

The reaction vessel used in the method of the present invention may be a single vessel, or may be a combination of two or more vessels which are fluid-communicated with each other. For example, the above-mentioned flow channel mixers (for example, the static fluid mixer, the press-fit-type mixer, the element-laminated mixer, and homomixer described above) can be used alone or two or more thereof can be used in combination. In a case where two or more reaction vessels are used in combination, the raw material solution and the silver salt solution containing the complex which are collected from the first reaction vessel are supplied to another reaction vessel together with one of more of an additional raw material solution, a silver salt solution, organic solvent for washing a silver salt solution, and organic solvent for diluting a raw material solution as needed, and the raw material solution and the silver salt solution are contacted with each other therein to further produce a PUFA-silver complex. This operation may be further repeated. Thereafter, the raw material solution and the silver salt solution are transferred to the distribution vessel (1), and the silver salt solution containing the PUFA-silver complex is collected.

Alternatively, the raw material solution and the silver salt solution containing the complex in the first reaction vessel are separated and collected in the first distribution vessel (1), then are supplied to another reaction vessel together with one of more of an additional raw material solution, silver salt solution, organic solvent for washing a silver salt solution, and organic solvent for diluting a raw material solution as needed, and are contacted with a new raw material solution to store the PUFA-silver complex. Then, the silver salt solution is separated and collected in another (second) distribution vessel (1) connected to the another reaction vessel This operation may be further repeated.

In any of the two or more reaction vessels, the temperature of the silver salt solution upon contact with the raw material solution or the organic solvent for washing the silver salt solution is preferably from 5° C. to 30° C. and more preferably from 15° C. to 30° C. As the organic solvent for washing the silver salt solution and the organic solvent for diluting the raw material solution, the same organic solvents as those used for diluting the raw material solution described above can be used. Preferably, the same organic solvent as used for diluting the raw material solution supplied to the first reaction vessel is used. The silver salt lution containing the collected PUFA-silver complex is transferred to an extraction vessel described later and subjected to a PUFA alkyl ester extraction step.

An example of the constitution of the reaction vessel will be described in more detail. The reaction vessel used in the method of the present invention may be a single vessel, or may be a combination of two or more vessels which are fluid-communicated with each other. For example, the above-mentioned flow channel mixers (for example, the static fluid mixer, the press-fit-type mixer, the element-laminated mixer, and homomixer described above) can be used alone or two or more mixers thereof can be used in combination. In a case where two or more reaction vessels are used in combination, the raw material solution and the silver salt solution containing the complex are supplied from the first reaction vessel to the next connected reaction vessel. There may be any number of reaction vessels, and one or more of these reaction vessels serve as the first reaction vessel. Thereafter, the raw material solution and the silver salt solution are transferred to the distribution vessel (1), and the silver salt solution containing the PUFA-silver complex and the raw material solution are collected. Alternatively, the silver salt solution and the raw material solution which have been transferred from the first reaction vessel to the first distribution vessel (1) and collected from the first distribution vessel (1) can he supplied to the second reaction vessel (composed of one or a plurality of reaction vessels). At this time, the raw material solution and the silver salt solution collected from the first distribution vessel (1) can be supplied to the second reaction vessel together with one of more of an additional raw material solution, silver salt solution, organic solvent for washing a silver salt solution, and organic solvent for diluting a raw material solution as needed. In the second reaction vessel, the raw material solution is contacted with the silver salt solution to further produce a PUFA-silver complex. Thereafter, the raw material solution and the silver salt solution are transferred to the first distribution vessel (1) or another (second) distribution vessel (1), and the silver salt solution containing the PUFA-silver complex and the raw material solution are collected. These operations may be further repeated. In a case where there are a plurality of the distribution vessels (1), the silver salt solutions containing the PUFA-silver complex which has been collected from the respective distribution vessels (1) may or may not be homogenized in a mixing vessel (for example, the above-mentioned flow channel mixer or a tank for simply mixing) for combining the solutions. The silver salt solution is transferred to an extraction vessel described later and subjected to a PUFA alkyl ester extraction step. Preferably, each reaction vessel has an inner diameter of 0.1 to 100 cm and a length of 0.05 to 10 m, and the silver salt solution in the reaction vessel has a linear velocity of 0.5 to 400 cm/sec and a retention time in the reaction vessel of about 0.02 to 300 sec, and, as needed, the raw material solution in the reaction vessel has a linear velocity of 0.5 to 400 cm/sec and a retention time in the reaction vessel of about 0.02 to 300 sec. More Preferably, each reaction vessel has an inner diameter of 0.3 to 43 cm and a length of 0.1 to 4 m, and the silver salt solution in the reaction vessel has a linear velocity of 0.5 to 400 cm/sec and a retention time in the reaction vessel of about 0.04 to 150 sec, and, as needed, the raw material solution in the reaction vessel has a linear velocity of 0.5 to 400 cm/sec and a retention time in the reaction vessel of about 0.04 to 150 sec. In addition, in a case where two or more reaction vessels are used in combination, the reaction vessel of the above conditions can be used.

In the organic phase (raw material solution) collected from the distribution vessel (1) a PUFA which has not been formed into a complex may be still contained. In this case, it is possible to supply the collected organic phase to the first or another reaction vessel and to contact the organic phase with the silver salt solution again, whereby the uncomplexed PUFA can be converted into a PUFA-silver complex, and thus the PUFA-silver complex can be collected together with the silver salt solution. The obtained silver salt solution can be collected by being transferred to the first distribution vessel (1) or another distribution vessel (1) together with the raw material solution and distributed from the organic phase. The collected silver salt solution can be combined with the silver salt solution containing the PUFA-silver complex obtained by the above-mentioned procedure, and can be subjected to a PUFA alkyl ester extraction step described later, or the collected silver salt solution alone can be subjected to the extraction step as well.

Preferably, the above procedure of the method of the present invention is performed under the hypoxic condition. The hypoxic condition can be achieved by, for example, blocking a system of the method of the present invention (for example, a reaction vessel (flow channel mixer), an supply channel, a collection channel, and a distribution vessel (1)) from external air to produce a closed system; by placing the inside of, for example, the reaction vessel, the supply channel, the collection channel, and the distribution vessel (1) under an inert gas atmosphere such as nitrogen; or by filling, for example, the reaction vessel, the supply channel, the collection channel, and the distribution vessel (1) with a liquid (raw material solution or silver salt solution). Preferably, the reaction vessel, the supply channel, the collection channel, and the distribution vessel (1) are blocked from the external air to produce a closed system and the closed system are filled with the raw material solution or the silver salt solution In a case where the supply to and collection from the reaction vessel of the silver salt solution and the raw material solution are both performed in the continuous mode, once the system is filled with the liquid, the low oxygen state can be maintained thereafter. Preferably, the hypoxic condition in the present invention refers to a condition where an oxygen concentration is less than 0.4%, and more preferably 0.1% or less. Also, preferably, the method of the present invention is performed under a light-shielded condition. When the method of the present invention is performed under the hypoxic condition and the light-shielded condition, a pH decrease of the silver salt solution and the oxidation of a fat or oil in the raw material solution and the silver salt solution can be suppressed and deterioration of the silver salt solution and deterioration of the purified PUFA-containing composition can be prevented.

(1-2. Extraction of PUFA Alkyl Ester)

A PUFA alkyl ester can be extracted from the silver salt solution containing a complex of PUFA and silver collected and is collected in the above-mentioned manner using an organic solvent. Therefore, the method for producing the PUFA-containing composition of the present invention may further include a step of extracting the PUFA alkyl ester from the silver salt solution collected from the reaction vessel using an organic solvent.

The procedure for extraction of the PUFA alkyl esters can be performed according to the conventional process such as the methods disclosed in Patent Literatures 1 to 4. More specifically, the silver salt solution containing the PUFA-silver complex collected from the reaction vessel is contacted with the organic solvent. The PUFA alkyl ester in the silver salt solution can be extracted into the organic solvent through this contact. The organic solvent which has been contacted with the silver salt solution is collected to thereby obtain the PUFA alkyl ester.

Examples of the organic solvent used for the extraction include solvents which have a high solubility of an alkyl ester (e.g., EPA, DHA and DPA) and can be separated from water, such as hexane, ether, ethyl acetate, butyl acetate, chloroform, cyclohexane, benzene, toluene, and xylene. Among them, hexane or cyclohexane is preferable.

Preferably, the silver salt solution collected from the reaction vessel is transferred to the extraction vessel for the purpose of contacting the silver salt solution with the organic solvent, and then is contacted with the organic solvent. The supply and collection of the silver salt solution or the organic solvent in the extraction vessel may be performed by the batch mode and is preferably performed in the continuous mode. Preferably, in the method of the present invention, the aqueous solution containing a silver salt collected from the reaction vessel and the organic solvent are supplied to the extraction vessel to contact them with each other, and then the organic solvent which has been contacted with the aqueous solution containing the silver salt is collected. Preferably, the supply of the aqueous solution containing the silver salt to the extraction vessel and the collection of the organic solvent are performed concurrently. More preferably, the supply of the organic solvent to the extraction vessel, the supply of the silver salt solution collected from the reaction vessel to the extraction vessel, the contact between the silver salt solution and the organic solvent, and the collection of the contacted organic solvent and the silver salt solution from the extraction vessel are performed concurrently.

The supply of the silver salt solution to the extraction vessel is performed via a flow channel through which the reaction vessel or the above-mentioned distribution vessel (1) (the above-mentioned mixing vessel, if necessary) is fluid-communicated with the extraction vessel (the flow channel is hereinafter also referred to as a "communication channel"). In addition, preferably, the supply of the organic solvent to the extraction vessel is performed via the flow channel through which the supply source of the organic solvent is fluid-communicated with the extraction vessel (the flow channel is hereinafter also referred to as an "organic solvent supply passage"). The communication channel and the organic solvent supply channel may be provided with, for example, a valve, a pump, and a valve. In addition, each of the communication channel and the organic solvent supply channel may be directly connected to the extraction vessel Alternatively, the communication channel and the organic solvent supply channel may be connected to each other collectively and then connected to the extraction vessel.

The temperature of the silver salt solution upon contact with the organic solvent is preferably from 30° C. to 80° C., and more preferably from 50° C. to 70° C. Examples of a method for maintaining the temperature of the silver salt solution within the above-mentioned range upon contact with the organic solvent include a method in which the silver salt solution and/or organic solvent are/is warmed to the above range and then these solutions are contacted with each other, a method in which the temperature of the extraction vessel is maintained with in the above-mentioned range, and a combination of these methods.

Preferably, the mixed solutions of the contacted silver salt solution and organic solvent are collectively collected from the extraction vessel. Then, the organic solvent containing the PUFA alkyl ester is fractionated from the collected mixed solution Preferably, the liquid collected from the extraction vessel is transferred to a distribution vessel (2) (a distribution vessel for distributing the organic solvent and the silver salt solution) in which is fluid-communicated with the extraction vessel, and the liquid is distributed to a phase of the organic solvent (organic phase) and a phase of the silver salt solution (aqueous phase) due to the specific gravity difference. When the distributed organic phase is fractionated, it is possible to collect the organic solvent containing the PUFA alkyl ester. Furthermore, when the distributed aqueous phase is fractionated, it is possible to collect the used silver salt solution Collection of the silver salt solution and the organic solvent from the distribution vessel (2) can be performed by the respective collection channels connected to the distribution vessel (2). In order to collect the distributed organic phase and aqueous phase easily, preferably, an outlet port of the silver salt solution from the distribution vessel (2) is arranged on the bottom surface or lower wall surface of the distribution vessel (2), and an outlet port of the organic solvent is arranged on the upper surface or upper wall surface of the distribution vessel (2). Also preferably, the silver salt solution may be suctioned from a nozzle arranged at a lower part, preferably on the bottom surface, of the distribution vessel (2) and collected from the distribution vessel (2), and the organic solvent may be tinned from the nozzle arranged at an upper part of the distribution vessel (2), and collected from the distribution vessel (2). The outlet ports and nozzles for the silver salt solution and the organic solvent in the distribution vessel (2) are connected to the respective collection channels. The collection channel may be provided with, for example, a valve, a pump, and a valve.

Preferred examples of the extraction vessel include the flow channel mixer provided separately from the reaction vessel. Examples of a flow channel mixer used for the extraction vessel include a flow channel mixer similar to that used for the above-mentioned reaction vessel, for example, a static fluid mixer, a press-fit-type mixer, an element-laminated mixer, and a homomixer described above (1-1). The extraction vessel may be a single vessel or may be a combination of two or more vessels which are fluid-communicated. For example, the static fluid mixer, the press-fit-type mixer, the element-laminated mixer, and the homomixer described above can be used alone or two more mixers thereof can be used in combination. In a case where two or more extraction vessels are used in combination, the organic solvent and the silver salt solution containing the complex which have been collected from the first extraction vessel are supplied to another extraction vessel together with an additional organic solvent and silver salt solution containing the complex as needed, and the organic solvent and the silver salt solution are contacted with each other therein to further form the PUFA. This operation may be further repeated. Thereafter, the organic solvent and the silver salt solution are transferred to the distribution vessel (2), and the organic solvent containing the PUFA is collected. Alternatively, the silver salt solution in the first extraction vessel is separated and collected in the distribution vessel (2), then is supplied to another extraction vessel together with an additional organic solvent and silver salt solution containing the complex as needed, and is contacted with a fresh organic solvent therein, and the PUFA remaining in the silver salt solution is extracted into the organic solvent. Then, the silver salt solution and the organic solvent are separated and collected in another (second) distribution vessel (2) connected to the another extraction vessel This operation may be further repeated. In any of the two or more extraction vessels, the temperature of the silver salt solution upon contact with the organic solvent is preferably from 30° C. to 80° C. and more preferably from 50° C. to 70° C.

In a case where the extraction vessel is a flow channel mixer, the linear velocity of the silver salt solution in the extraction vessel is preferably 0.5 cm/sec or more, and more preferably from 0.5 to 400 cm/sec. More preferably, the linear velocity of the silver salt solution and the organic solvent in the extraction vessel is 0.5 cm/sec or more, and more preferably from 0.5 to 400 cm/sec, respectively. When the linear velocity of the silver salt solution is low, the efficiency of PUFA alkyl ester extraction into the organic solvent is reduced, and the yield of the desired PUFA is reduced. On the other hand, when the linear velocity of the silver salt solution and the organic solvent is high, there is a possibility that the separation may fail in a distribution vessel (2), and the internal pressure of the extraction vessel increases, thereby increasing the risk of damage. The retention time of the silver salt solution in the extraction vessel preferably about from 0.02 to 300 seconds, and more preferably about from 0.04 to 150 seconds. More preferably, the retention time of the silver salt solution and the organic solvent in the extraction vessel is about from 0.02 to 300 seconds, and more preferably about from 0.04 to 150 seconds. Preferably, each extraction vessel has an inner diameter of 0.1 to 100 cm and a length of 0.05 to 10 m, and the silver salt solution in the extraction vessel has linear velocity of 0.5 to 400 cm/sec and a retention time in the extraction vessel of about 0.02 to 300 sec, and, as needed, the organic solvent in the extraction vessel has a linear velocity of 0.5 to 400 cm/sec and a retention time the reaction vessel of about 0.02 to 300 sec. Preferably, each extraction vessel has an inner diameter of 0.3 to 43 cm and a length of 0.1 to 4 m, and the silver salt solution in the extraction vessel has a linear velocity of 0.5 to 400 cm/sec and a retention time in the extraction vessel of about 0.04 to 150 sec, and, as needed, the organic solvent in the extraction vessel has a linear velocity of 0.5 to 400 cm/sec and a retention time in the extraction vessel of about 0.04 to 150 sec. In addition, in a case where two or more extraction vessels are used in combination, the extraction vessel of the above conditions can be used.

In order to prevent oxidation of the extracted PUFA alkyl ester and the fat or oil in the silver salt solution, it is preferable to perform the above PUFA alkyl ester extraction procedure also under the hypoxic condition or under light shielded condition. Preferably, the system of the procedure (for example, the extraction vessel, the communication channel, the organic solvent supply channel, the collection channel, and the distribution vessel (2)) is placed under the hypoxic condition or the light shielded condition. The hypoxic condition can be achieved by the same procedure as the procedure described in the above (1-1).

(1-3. Prevention of Deterioration of Silver Salt Solution and Re-Use Thereof)

In the method for producing the PUFA-containing composition of the present invention, a decrease in a pH value of the silver salt solution, oxidation of an oil or fat in the raw material solution and the silver salt solution, deterioration of the silver salt solution thereby, and deterioration of a purified PUFA-containing composition can be greatly prevented by performing processes of supply and collection of the silver salt lution in the reaction vessel (flow channel mixer), and further a process of supply and collection of the silver salt solution in the extraction vessel, as needed, concurrently and continuously (that is, in a continuous mode), preferably, by performing processes starting from the supply of the silver salt solution to the reaction vessel until the collection of the silver salt solution from the extraction vessel in a continuous mode. For example, in the conventional batch mode, it is considered that the fat or oil incorporated in the silver salt solution is oxidized during a process of stirring and mixing the raw material solution and the silver salt solution in the reaction vessel, and the batch collection of the silver salt solution after the reaction, which results in deterioration of the silver salt solution. On the other hand, in the continuous mode as in the present invention, since the contact between the silver salt solution and the outside air can be extremely reduced in the reaction vessel or the extraction vessel or during the process of collection of the silver salt solution therefrom, deterioration of the silver salt solution can be suppressed.

Therefore, in the method of the present invention, the silver salt solution collected from the extraction vessel can be reused. More specifically, in the method of the present invention, the silver salt solution collected from the extraction vessel can be supplied to the reaction vessel again directly or after being appropriately adjusted for the concentration of the silver salt, thereby being contacted with the raw material solution In a preferred embodiment of the method of the present invention, the silver salt solution to be supplied to the reaction vessel contains the silver salt solution collected from the extraction vessel after the contact with the organic solvent.

Therefore, in a preferred embodiment, the method for producing the PUFA-containing composition of the present invention can be a method in which the contact of the silver salt solution with the raw material solution and the contact of a silver salt solution containing a complex thus produced with the organic solvent are performed continuously while circulating the silver salt solution between the reaction vessel and the extraction vessel. In this method, the silver salt solution collected from the reaction vessel is contacted with the organic solvent a PUFA alkyl ester is extracted from the silver salt solution, and then the silver salt solution which has been contacted with the organic solvent is collected from the extraction vessel, and supplied to the reaction vessel again. The silver salt solution which has been supplied to the reaction vessel again is contacted with the raw material solution to form a PUFA-silver complex. In the method of the present invention, the silver salt solution can be repeatedly used preferably 10 times or more, more preferably 30 times or more, still more preferably 70 times or more, still more preferably 100 times or more, and still more preferably 300 times or more. In the present invention, the term "use" as used herein in relation to the repeated use of the silver salt solution refers to a series of processes starting from the supply of the silver salt solution into the reaction vessel and until the collection thereof from the extraction vessel, and the phrase "the series of processes is carried out one round" corresponds to that the silver salt solution is used "once". In one round of the processes, the time during which the silver salt solution is contacted with the PUFA (PUFA contact time as mentioned in the Example described later, that is, the time between a time point at which the silver salt solution is supplied to the raw material solution and a time point at which a PUFA ethyl ester-containing composition is extracted from the silver salt solution using an organic solvent) is preferably 10 minutes or shorter, and more preferably 5 minutes or shorter on average.

The degree of deterioration of the silver salt solution can be measured using, for example, a pH value or color of the silver salt solution, an amount of free fatty acid contained in the silver salt solution, or the Gardner color scale of the solution as an index. For example, an unused silver salt solution usually has a pH value of about 7, is colorless and transparent, and contains no free fatty acid. However, when the silver salt solution is deteriorated with an increased use, it is reduced in the pH value thereof, is disclosed into yellowish to brownish color, and is increased in the amount of free fatty acids. The amount of the free fatty acids in a solution can be measured by the method described in Reference Example 2 described later. According to the method of the present invention, the amount of the free fatty acids in the silver salt solution that has been used repeatedly in 10 rounds of the series of process for forming a complex and extracting PUFA alkyl ester can be reduced to preferably 5 mEq/L or less, and more preferably 3 mal/L or less. Still more preferably, the amount of the free fatty acid in the silver salt solution used repeatedly in 100 rounds of the series of processes can be reduced to preferably 50 mEq/L or less, and more preferably 20 mEq/L or less.

The Gardner color scale of the silver salt solution can be measured in accordance with Japanese Industrial Standards, JIS K0071 "Testing Method for Color of Chemical Products". A higher Gardner color scale of a solution means that the silver salt solution is further deteorated. The Gardner color scale of the silver salt solution used in the method of the present invention is about 5 even after used repeatedly about 30 times or and is never 9 or more even after used further repeatedly. In contrast, the Gardner color scale of the silver salt solution that is used in the conventional batch method is increased to 11 or more when used repeatedly about 15 times. These results mean that the silver salt solution is hardly deteriorated in the method of the present invention, as compared with a batch method.

In the method for producing the PUFA-containing composition according to the present invention, a continuous mode is employed and the silver salt solution is re-used, and therefore it becomes possible to reduce the amount of the silver salt solution required for extraction of a PUFA, as compared with the conventional method (a batch-mode). In a preferred embodiment, in the method according to the present invention, the amount of the silver salt solution which is required for the extraction of a PUFA can be reduced to about 1/2 to 1/20, preferably about 1/5 to 1/10, as compared with the conventional method.

(1-4. Separation of PUFA-Containing Composition)

In the present invention, the organic solvent containing a PUFA alkyl ester collected by the above procedure can be obtained as a PUFA-containing composition. The PUFA-containing composition contains an alkyl ester of PUFA, preferably EPA, DHA, or DPA, separated from the raw material solution. The collected organic solvent may be further purified by, for example, concentration, chromatography, distillation, as necessary. The PUFA-containing composition obtained by the method of the present invention preferably contains an alkyl ester of at least one PUFA selected from the group consisting of EPA, DHA, and DPA, more preferably contains an alkyl ester of EPA and/or DHA, in an amount of 70% by mass or more, and preferably 50% by mass or more, and sill more preferably contains an alkyl ester of EPA in an amount of 50% by mass or more, and more preferably 70% by mass or more, in the total fatty acids contained. More preferably, the PUFA-containing composition obtained by the method of the present invention contains an alkyl ester of EPA and an alkyl ester of DHA in an amount of 70% by mass or more, and preferably 80% by mass or more in total, and contains an EPA alkyl ester in an amount of 55% by mass or more, and preferably 60% by mass or more, in the total fatty acids contained.

In the method of the present invention the collected organic solvent from which a PUFA alkyl ester is separated by, for example, concentration, chromatography, distillation can be re-used for extraction of a PUFA alkyl ester. More specifically, the organic solvent from which the PUFA alkyl ester has been separated can be supplied to the extraction vessel again directly or after being mixed with a fresh organic solvent, thereby being contacted with the silver salt solution.

In the method for producing a PUFA-containing composition by the continuous mode according to the present invention, it is not necessary to collect the silver salt solution containing the complex or a batch of the organic solvent containing a PUFA as in the conventional method (batch mode), and there is no need to halt the complex production reaction or the PUFA extraction operation. In the method of the present invention, deterioration of the silver salt solution can be suppressed, and the amount of the silver salt solution used can be reduced. Thus, the present invention provides a highly efficient and low cost PUFA producing method.

(2. Apparatus for Producing PUFA-Containing Composition)

As a preferred embodiment of the present invention, a schematic diagram of the procedure for producing a PUFA-containing composition using flow channel mixers in the reaction vessel and the extraction vessel is disclosed in FIG. 1.

In FIG. 1, the flow channel mixers of the reaction vessel and the extraction vessel are the same-type concurrent flow static fluid mixer and are internally provided with a blade for fluid mixing. The flow channel mixer is fluid-communicated with a raw material solution supply source and a silver salt solution supply source. The raw material solution and the silver salt solution supplied to the reaction vessel are mixed by the stirring action of the blade and contacted with each other. By adjusting the amounts of the raw material solution and the silver salt solution to be stirred, liquid droplets of the raw material solution or the silver salt solution can be produced. In one embodiment, the raw material solution in the reaction vessel is a continuous phase, and the silver salt solution is in a form of liquid droplets. In another embodiment, the raw material solution in the reaction vessel is in a form of liquid droplets, and the silver salt solution is a continuous phase. In another embodiment, the raw material solution and the silver salt solution in the reaction vessel are both in the continuous phase. Since the reaction vessel is communicated with the distribution vessel (1) on the opposite side of a liquid charging port, the liquid supplied to the reaction vessel is gradually transferred to the distribution vessel (1). In the distribution vessel (1), the raw material solution (organic phase) is separated as an upper layer, and the complex-containing silver salt solution (aqueous phase) is separated as a lower layer. The raw material solution on the upper layer is collected, and the silver salt solution on the lower layer is transferred to the extraction vessel.

In FIG. 1, the extraction vessel is fluid communicated with the lower layer of the distribution vessel (1) and the organic solvent source. The organic solvent and the silver salt solution supplied to the extraction vessel are mixed by the stirring action of the blade so as to contact with each other. In one embodiment, the organic solvent in the extraction vessel is a continuous phase, and the silver salt solution is in a form of liquid droplets. In one embodiment, the organic solvent in the extraction vessel is in a form of liquid droplets and the silver salt solution is a continuous phase. In another embodiment, the organic solvent and the silver salt solution in the extraction vessel are both in a continuous phase. The extraction vessel is communicated with the distribution vessel (2) on the opposite side of the liquid inlet port, and therefore the liquid supplied to the extraction vessel is gradually transferred to the distribution vessel (2). In the distribution vessel (2), the organic solvent containing PUFA (organic phase) is separated as an upper layer, and the silver salt solution (aqueous phase) as a lower layer. The upper organic solvent is collected and the PUFA-containing composition is purified or concentrated. The silver salt solution, on the lower layer is returned to the silver salt solution supply source and is then supplied to the reaction vessel again.

In FIG. 1, the reaction vessel, the extraction vessel, the distribution vessel, and the flow channel connecting these vessels are a closed system and are filled with a liquid. As illustrated in FIG. 1, the internal temperature the reaction vessel and the extraction vessel can be controlled by means of a cooling medium or a heating medium provided therein. Also as illustrated in FIG. 1, the speed and amount of a liquid to be supplied to and collected from the reaction vessel and the extraction vessel can be controlled by means of a pump. The linear velocity of the silver salt solution and the raw material solution in the reaction vessel and the extraction vessel is preferably about from 0.5 to 400 cm/sec. Preferably, the temperature of the silver salt solution in the reaction vessel is from 5° C. to 30° C. Preferably, the temperature of the silver salt solution in the extraction vessel is from 30° C. to 80° C.

In a preferred embodiment, the PUFA contact time of the silver salt solution in the apparatus of FIG. 1 is preferably 10 minutes or shorter, and more preferably 5 minutes or shorter per use on average. As illustrated in FIG. 1, in the method for producing the PUFA-containing composition used in the present invention, the supply and collection of the silver salt solution in the reaction vessel and the extraction vessel are performed concurrently and continuously, the PUFA-containing composition to thereby achieve the continuous extraction, and thus it does not require a large scale reaction vessel as employed in the conventional batch mode. According to the present invention, it is possible to miniaturize a facility needed for the PUFA production.

EXAMPLES

Hereinafter, the present invention will be described in more detail by way of examples, but the present invention is not limited to these examples.

Reference Example 1

Analysis of Compositional Ratio of Fatty Acid

A measurement sample in an amount of 12.5 mg was diluted in 1 mL of n-hexane, and the resultant solution was analyzed for the content ratio of each fatty acid in the total fatty acids using a gas chromatography analysis apparatus (Type 7890 GC; manufactured by Agilent Technologies) under the following conditions. The results were expressed as % by mass each. converted from the area of a chromatogram.

<Inlet Part Condition>
Inlet port temperature: 250° C., Split ratio: 10
<Column Condition>
Column: DB-WAX, manufactured by J & W Scientific: 0.25 mm×30 m, Column tempature: 210° C.
He flow rate: 1.0 mL/min, He pressure: 20 PSI
<Detection Condition>
$H_2$ flow rate: 40 mL/min, Air flow rate: 450 mL/min
He flow rate: 1.00 mL/min, DET temperature: 260° C.

The fatty acids analyzed are as follows: AA-E: arachidonic acid ethyl ester, DPA-E: docosapentaenoic acid ethyl ester, DNA-E: docosahexaenoic acid ethyl ester, ETA-E: eicosatetraenoic acid ethyl ester, EPA-E: eicosapentaenoic acid ethyl ester.

Reference Example 2

Method for Measuring Free Fatty Acid Content in Silver Salt Solution 1. Preparation of standard solution (1) Myristic acid in an amount of 0.114 g was placed in a 100 mL measuring flask, and was then diluted to 100 mL with dimethyl sulfoxide.

(2) Triethanolamine in an amount of 1.5 g was separately placed in a 100 mL measuring flask, and was then diluted to 100 mL with pure water.

(3) Tetrasodium ethylene diaminetetraacetic acid tetrahydrate in an amount of 0.10 g was separately placed in a 100 mL measuring flask, and was then diluted to 100 mL with pure water.

(4) The solution prepared in (1) in an amount of 20 mL, the solution prepared in (2) in an amount of 10 mL, and the solution prepared in (3) in an amount of 10 mL were placed in a 100 mL measuring flask, and were then diluted to 100 mL with pure water to obtain a standard solution.

2. Preparation of Copper Sample Solution (1) Copper (II) sulfate pentahydrate in an amount of 6.49 g and sodium chloride in an amount of 20.0 g were placed in a beaker, and then were dissolved with pure water, then the resultant solution was transferred to a 100 mL measuring flask, and was then combined with a wash solution of beaker', and the resultant solution was diluted to 100 mL with pure water.

(2) Triethanolamine in an amount of 14.9 g was separately placed in a 100 mL measuring flask, and was then diluted to 100 mL with pure water.

(3) The same amount (volume ratio) of the solution prepared in (1) and the solution prepared in (2) were mixed together to obtain a copper sample solution.

3. Preparation of Color-Developing Sample Solution

Bathocuproine in an amount of 0.189 g was placed in a 250 mL measuring flask, and was then diluted to 250 mL with 2-butanol.

4. Operation Procedure (1) Each of silver salt solution in an amount of 5 µL and the standard solution in an amount of 500 µL was placed in a capped test tube, and then 1 mL of a copper sample solution was added thereto.

(2) A chloroform/heptane mixed solution (1/1 by volume) in an amount of 3 mL was added to each test tube, and each of the test tubes was capped, and was shaken vigorously by hand for 3 minutes.

(3) After the shaking, the cap was removed and centrifugation (3,000 rpm) was performed.

(4) A supernatant in an amount of 2 mL was collected, and was placed in another test tube, then the color-developing sample solution in an amount of 2 mL was added to the test tube, and then the resultant solution was shaken gently.

(5) After 2 to 3 minutes, the absorbance at 475 nm was measured using pure water as a control.

5. Calculation Formula

The concentration of a free fatty acid in the silver aqueous solution was calculated by the following Formula (1).

$$\text{Free fatty acid concentration (meq/L)} = (B/A) \times (D/C) \quad \text{(Formula 1)}$$

A: Absorbance obtained using a standard solution
B: Absorbance obtained using a sample solution.
C: Amount of sample collected (µL)
D: Amount of standard solution collected (µL)

Reference Example 3

Method of Measuring Silver Salt

The amount of silver salt in the silver salt solution and the raw material solution was measured by atomic absorption spectrometry according to JIS K 0121.

Reference Example 4

Method of Measuring Linear Velocity of Silver Salt Solution

The linear velocity of the silver salt solution in the reaction vessel and the extraction vessel was calculated from the length of the reaction vessel or the extraction vessel and the time required for the silver salt solution to pass through, the reaction vessel or the extraction vessel.

Linear velocity of silver salt solution (cm/sec)
=[Length of reaction vessel or extraction vessel (cm)]/ [time required for silver salt solution to pass through reaction vessel or extraction vessel (sec)]

Time required for the silver salt solution to pass through the reaction vessel or extraction vessel (sec)
=[Volume of silver salt solution in reaction vessel or extraction vessel (mL)]/[flow velocity of silver salt solution in reaction vessel or extraction vessel (mL/sec) ]

(Material)
Raw material oil: AA-E 2.5%, ETA-E 1.7%, EPA-E 44.5%,
DPA-E 2.1%, DHA-E 7.4%,
Peroxide value (POV)=1.0 mEq/kg,
Acid value (AV)=0.1 mg/g
Silver salt solution: 50% by mass of silver nitrate aqueous solution
Organic solvent: cyclohexane
Reaction vessel and Extraction vessel: concurrent flow type flow channel mixer (static mixer, model number T3-27-2PT, inner diameter 3.4 mm, length 15.5 cm; manufactured by Noritake Co., Ltd.)

Example 1

A PUFA ethyl ester was purified from the raw material oil in a continuous mode. A raw material solution was obtained by mixing and dissolving 30 g of raw material oil with respect to 14 mL of organic solvent. The raw material solution and the silver salt solution thus obtained were each cooled to 15° C., and pressed into a reaction vessel from respective supply channels connected to one end (supply port) of the reaction vessel (flow channel mixer), and were contacted with, each other in the reaction vessel. The silver salt solution in an amount of 120 g was flowed thereto from the supply channel at a flow rate of 30 g/min, and the raw material solution in an amount of 41 g was flowed thereto from the supply channel at a flow rate of 10.3 g/min. The linear velocity of the silver salt solution flowing in the reaction vessel was 7.5 cm/sec, and the retention time of the silver salt solution in the reaction vessel was 2 seconds. The temperature in the reaction vessel was 20° C.

An end on the side opposite (collection port) of the reaction vessel was directly connected to a distribution vessel (1), and an aqueous phase (the silver salt solution containing the PUFA-silver complex) was accumulated in the lower part of the distribution vessel (1). The retention time of the aqueous phase in the distribution vessel (1) was 2.1 minutes. The aqueous phase was pressed into an extraction vessel at a flow rate of 33 g/min from a supply channel connected to one end of the extraction vessel (another flow channel mixer). The linear velocity of the aqueous phase in the extraction vessel was 14 cm/sec. Concurrently, organic solvent in an amount of 140 mL heated to 65° C. was flowed thereto from the supply channel connected to the same end of the extraction vessel at a flow rate of 35 mL/min, and the aqueous phase and the organic solvent are contacted with each other in the extraction vessel so that the PUFA ethyl ester in the aqueous phase was extracted into the organic solvent. The temperature in the extraction vessel was 60° C., and the retention time of the aqueous phase in the extraction vessel was 1 second. An end on the side opposite (collection port) of the extraction vessel was directly connected to a distribution vessel (2), and the aqueous phase (silver salt solution) accumulated in the lower part of the distribution vessel (2) was separated from the organic phase to be collected. The organic phase was separately collected from the distribution vessel (2), and the organic solvent was distilled off to obtain a PUFA ethyl ester-containing composition. A part of the aqueous phase (silver salt solution) collected from the distribution vessel (2) was subjected to measurement for the free fatty acid content, and the rest was re-used. A series of steps as mentioned above was defined as one process and the process was repeated 10 times. The total retention time of the aqueous phase (silver salt solution) in the reaction vessel, the distribution vessel (1), and the extraction vessel per process was calculated as the contact time between the silver salt solution and the raw material solution to obtain an average value over 10 processes. The raw material solution and the organic solvent were replaced with fresh ones for each process. During the process, the supply channels, the reaction vessel, the extraction vessel, the distribution vessels (1) and (2), and the flow channels which are communicated with them are constantly filled with a liquid (raw material solution, silver salt solution, or organic solvent), and all the operations were performed under the hypoxic conditions.

Comparative Example 1

A PUFA ethyl ester was purified from the raw material oil by a batch mode. The raw material oil in an amount of 30 g was well mixed with 14 mL of an organic solvent, and dissolved to obtain a raw material solution Silver salt solution in an amount of 120 g and raw material solution in an amount of 41 g were introduced in a flask and the resultant solution was stirred under a nitrogen atmosphere (oxygen concentration of 0.4%) at 20° C. for 20 minutes at a speed of 300 rpm. The obtained solution after stirring was allowed to stand still at 20° C. for 15 minutes, then a separated organic phase was removed, and then an aqueous phase (silver salt solution containing a PUFA-silver complex) was collected. The obtained aqueous phase was heated to 60° C., then 140 mL of organic solvent was added thereto, and the resultant solution was stirred at a speed of 300 rpm for 20 minutes under the condition of 60° C., and a PUFA ethyl ester in the aqueous phase was extracted into the organic phase. The liquid obtained after stirring was allowed to stand still, and then a separated organic phase was collected and then concentrated to obtain a PUFA ethyl ester-containing composition. The remaining aqueous phase (silver salt solution) was collected, and a part thereof was subjected to measurement for the free acid content, and the rest was reused. A series of steps as mentioned above was defined as one process, and the process was repeated ten times each time using fresh raw materials per process. The time from the mixing of the raw material solution and the silver salt solution to the separation of the organic phase containing PUFA ethyl ester per process was calculated as the time for contact between the silver salt solution and the raw material solution, and the average value over 10 processes was determined.

Test Example 1

Fatty Acid Composition and Yield of PUFA-Containing Composition

The fatty acid composition of the raw material oil, the PUFA-containing compositions obtained in Example 1 and Comparative Example 1, and the yield of the PUFA-containing composition obtained in Example 1 and Comparative Example 1 were measured according to Reference Example 1. The results are indicated in Table 1.

TABLE 1

| | | Fatty acid composition (%) | | | | |
|---|---|---|---|---|---|---|
| | Yield (g) | C20:4 (n − 6) | C20:4 (n − 3) | C20:5 | C22:5 | C22:6 |
| Raw material oil | — | 2.5 | 1.7 | 44.5 | 2.1 | 7.4 |
| PUFA-containing (composition Example 1) | 11.4 | 0.2 | 0.3 | 76.4 | 1.8 | 15.0 |
| PUFA-containing composition (Comparative Example 1) | 11.5 | 0.2 | 0.3 | 76.3 | 1.8 | 15.2 |

Test Example 2

Acid Value (AV)

The acid value (AV value) of each of 10 samples of the PUFA-containing composition obtained in each process of Example 1 and Comparative Example 1 was measured, and the average value of the 10 samples was obtained. In addition, the acid value (AV value) of the raw material solution was measured. The results are indicated in Table 2.

Test Example 3

Amount of Silver Nitrate in Silver Salt Solution

The amount of silver nitrate in the raw material solution after being used in each process of Example 1 and Comparative Example 1 was measured according to Reference Example 3. Based on the amount of silver nitrate the silver salt solution before use, the amount of silver nitrate (loss rate) transferred to the raw material solution and lost was calculated. The results are indicated in Table 2 as an average value of 10 samples.

TABLE 2

|  | Contact time between silver salt solution and raw material solution (Min) | Acid value (AV) | | Amount of silver nitrate | | |
|---|---|---|---|---|---|---|
|  |  | Raw material solution | PUFA-containing composition | In silver salt solution before use (g) | In raw material solution after use (mg) | Loss rate (%) |
| Example 1 | 2.1 | 0.1 | 0.6 | 60 | 1.62 | 0.0027 |
| Comparative Example 1 | 60 | 0.1 | 1.8 | 60 | 51.0 | 0.085 |

As indicated in Table 1, the yield of the PUFA-containing composition obtained by the method of Example 1 and the fatty acid composition thereof were equivalent to those in the conventional batch method (Comparative Example 1). On the other hand, as indicated in Table 2, even in a case where the same amount of the raw material oil is treated, an increase in the acid value of the PUFA-containing composition was suppressed in the method of Example 1, as compared to the conventional batch method (Comparative Example 1). It is considered that in the method of Example 1, since the time for contact between the raw material solution and the silver salt solution was able to be further shortened, an increase in the acid value of the PUFA-containing composition was able to be suppressed. Therefore, it was found that the method of the present invention can provide a PUFA-containing composition having excellent quality without lowering the yield, as compared to the conventional method Further, in the method of Example 1, the loss rate of silver nitrate was significantly reduced as compared to the conventional method (Comparative Example 1), and the utilization efficiency of the silver salt solution was able to be significantly improved.

Test Example 4

Relationship Between Linear Velocity of Silver Salt Solution and PUFA Yield

A PUFA-containing composition was produced in the same manner as in Example 1, except that the linear velocity of the silver salt solution in the reaction vessel was changed as indicated in Table 3. In addition, a PUFA-containing composition was produced in the same procedure as in Example 1 by changing the size of the reaction vessel and the extraction vessel to have an inner diameter of 8 mm and a length of 26 cm (Example 10). The fatty acid composition of the obtained PUFA-containing composition was measured according to Reference Example 1, and the EPA-E content (96) in the composition and the EPA-E collection rate (%) from the raw material oil were calculated. The results are indicated in Table 3.

TABLE 3

|  | Linear velocity of silver salt solution (cm/sec) | | Retention time (sec) | | PUFA-containing composition | | | |
|---|---|---|---|---|---|---|---|---|
|  |  |  |  |  |  | EPA-E | | DHA-E |
| Example | Reaction vessel | Extraction vessel | Reaction vessel | Extraction vessel | Yield (%) | Content (%) | Collection rate (%) | Content (%) |
| 2 | 0.2 | 0.2 | 77.50 | 77.50 | 10.5 | 75.0 | 16.6 | 18.0 |
| 3 | 0.5 | 0.5 | 31.00 | 31.00 | 29.2 | 75.2 | 57.2 | 17.8 |
| 4 | 0.67 | 0.67 | 23.13 | 23.13 | 30.0 | 75.2 | 59.3 | 17.8 |
| 5 | 10.1 | 10.1 | 1.53 | 1.53 | 36.3 | 75.7 | 62.3 | 16.5 |
| 6 | 15.1 | 15.1 | 1.03 | 1.03 | 38.2 | 76.0 | 65.8 | 16.1 |
| 7 | 18 | 18 | 0.86 | 0.86 | 38.3 | 75.6 | 65.6 | 16.4 |
| 8 | 137 | 137 | 0.11 | 0.11 | 40.6 | 74.8 | 67.1 | 15.6 |
| 9 | 400 | 400 | 0.04 | 0.04 | 41.0 | 74.5 | 67.5 | 15.2 |
| 10 | 23.5 | 23.5 | 1.11 | 1.11 | 38.0 | 75.7 | 65.6 | 16.5 |

As indicated in Table 3, when the linear velocity of the silver salt solution supplied to the reaction vessel was 0.5 cm/sec or more, the content of EPA-E of the obtained PUFA-containing composition was high, and EPA-E was also able to be purified from the raw material oil to achieve a collection rate as high as 57% or more.

Test Example 5

Relationship Between Treatment Time and Silver Salt Solution Deterioration

The PUFA contact time of the silver salt solution per process and the average value (for 10 processes) of the increase in FFA content in the silver salt solution after use in Example 1 and Comparative Example 1 are indicated in Table 4.

TABLE 4

|  | Average total contact time (Min) | Average FFA increase (mEq/L) |
|---|---|---|
| Example 1 | 2.1 | 0.13 |
| Comparative Example 1 | 60 | 1.21 |

Test Example 6

Deterioration of Silver Salt Solution (Color Change)

In Example 1 and Comparative Example 1, the appearance and color (Gardner color scale) of a silver salt solution used repeatedly 10 processes were compared. A Gardner color scale of the solution was evaluated by performing a sensory test in which the solution was compared to a Gardner standard solution with naked eyes by three persons and adopting the average value thereof. The results are indicated in Table 5.

TABLE 5

|  | Appearance | Gardner color scale |
|---|---|---|
| Example 1 | Light yellow | 2 |
| Comparative Example 1 | Yellow | 9 |

As indicated in Table 4, the FFA content in the silver salt solution was increased with PUFA contact time. In Example 1 using the continuous mode, as compared to Comparative Example 1 using the batch mode, the PUFA contact time of the silver salt solution became shorter, and an increase in the FFA content was also suppressed. Further, as indicated in Table 5, in Example 1, the color change of the silver salt solution was smaller than that in Comparative Example 1. From this, it was shown that deterioration of the silver salt solution was suppressed in Example 1.

Test Example 7

Figure 2:
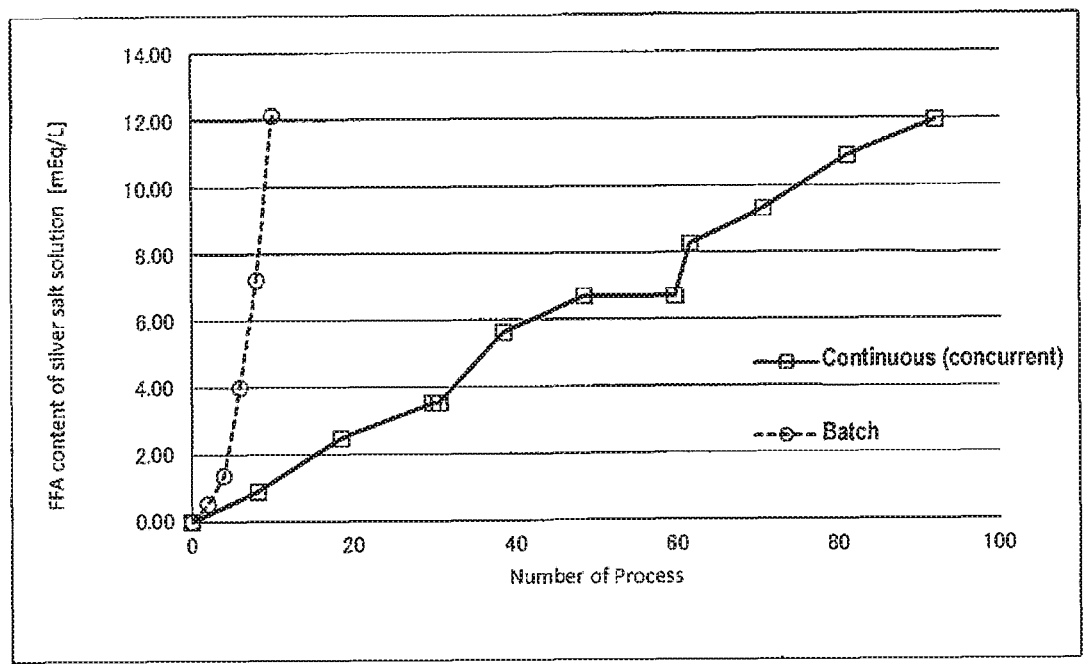
FIG. 2 illustrates a change over time in a free fatty acid content with repeated use of a silver salt solution.

Comparison of Deterioration Level (Free Fatty Acid Content) of Silver Salt Solution In the same procedure as in Example 1 and Comparative Example 1, the process of PUFA ethyl ester purification was repeated. The free fatty acid (FFA) content in the silver salt solution after use was measured according to Reference Example 2 after several processes. The temporal change of the free fatty acid (FFA) content with the number of repeated uses (number of processes) of the silver salt solution are illustrated in FIG. 2.

Test Example 8

Relationship Between Amount of Silver Salt Solution Used and PUFA Yield

In the same procedure as Example 1 and Comparative Example 1, the process of PUFA ethyl ester purification was repeated until the FFA content in the silver salt solution exceeded 10 mEq/L. The cumulative yield of the obtained PUFA-containing composition is indicated in Table 6. In the continuous mode as in. Example 1, the yield of the PUFA-containing composition was increased by 8 times or more as compared to the batch mode as in Comparative Example 1. From this, it was found that in the continuous mode as in Example 1, deterioration of the silver salt solution can be suppressed to thereby use the silver salt solution repeatedly, and accordingly, the amount of the silver salt solution necessary for producing the PUFA-containing composition can be significantly reduced as compared to the batch mode.

TABLE 6

|  | | Until FFA content of the silver salt solution exceeded 10 mEq/L | |
|---|---|---|---|
|  | Total amount of silver salt solution used (g) | Number of processes (Num) | PUFA-containing composition yield (g) |
| Example 1 | 120 | 78 | 890 |
| Comparative Example 1 | 120 | 9 | 104 |

Test Example 9

Relationship Between Raw Material Solution POV and Silver Salt Solution Deterioration The influence of the oxidation deterioration of the raw material oil on the deterioration of the silver salt solution was investigated. The PUFA ethyl ester purification was performed according to Example 1 using the following raw material oils A to D different in oxidation index (POV and AV). Further, PUFA ethyl ester purification was performed according to Comparative Example 1 using the following raw material oils C to D. The change in FFA content in the silver salt solution after three times repeated use (3 processes) was investigated. The results are indicated in Table 7.

Raw material oil A: POV=1.0 mEq/kg, AV=0.2 mg/g

Raw material oil B: POV=11.6 mEq/kg, AV=0.1 mg

Raw material oil C: POV=40.5 mEq/kg, AV=0.2 mg

Raw material oil D: POV=1.3 mEq/kg, AV=5.3 mg (In all of these raw material oils, the fatty acid composition was as follows: AA-E 2.8%, ETA-E 1.8%, EPA-E 44.7%, DPA-E 2.0%, DHA-E 7.7%)

TABLE 7

| Purification method | Raw material oil | POV (mEq/kg) | AV (mg/g) | FFA content of silver salt solution (mEq/L) | |
|---|---|---|---|---|---|
| | | | | Before use (0 process) | After use three times (three processes) |
| Example 1 | A | 1.0 | 0.2 | 0.2 | 1.0 |
| | B | 11.6 | 0.1 | 0.1 | 3.3 |
| | C | 40.5 | 0.2 | 0.0 | 5.9 |
| | D | 1.3 | 5.3 | 0.0 | 9.8 |
| Comparative Example 1 | C | 40.5 | 0.2 | 0.0 | 58.6 |
| | D | 1.3 | 5.3 | 0.0 | 25.0 |

Test Example 10

Deterioration Level of Silver Salt Solution in PUFA Ethyl Ester Purification by Continuous Mode Using Counter Current Flow (Material)

Raw material oil: AA-E 2.6%, ETA-E 1.7%, EPA-E 44.5%,

DPA-E 2.1%, DHA-E 7.4%,

Peroxide value (POV)=1.0 mEq/kg,

Acid value (AV)=0.1 mg/g

Silver salt solution: 50% by mass of silver nitrate aqueous solution

Organic solvent: cyclohexane

Reaction vessel and Extraction vessel: Countercurrent flow type flow channel mixer. The silver salt solution is supplied from the upper part of the column filled with the organic phase, and settled in the column while being made more fine by a vibrator to be contacted with the organic phase. The column (inner diameter of 20 mm, length of 20 cm, cylindrical type) has the silver salt solution supply port (nozzle, inner diameter of about 1 mm), the tip of which is located within 2 cm below the top surface of the organic phase (raw material solution, organic solvent) and the silver salt solution collection port is located at a lower part of the column.

The raw material oil in an amount of 30 g was mixed with organic solvent in an amount of 14 mL and dissolved to thereby obtain a raw material solution The obtained raw material solution in an amount of 47 mL was packed into the first column (reaction vessel), and argon gas was blown from the upper part to purge air in the column (i oxygen concentration in column: 0.1% or less). From the supply port in the column, 120 g of silver salt solution was added dropwise at a flow rate of 10 g/min to contact raw material solution and the silver salt solution with each other. The silver salt solution to be added dropwise was made more fine with a vibrator. Concurrently with the dropwise addition of the silver salt solution, an aqueous phase accumulated in the lower part of the column was collected at a rate of 11 g/min. The distance between the nozzle tip of the supply port of the column and the top surface of the aqueous phase was maintained at 13 cm. The linear velocity of the silver salt solution flowing in the reaction vessel was 0.1 /sec, and the retention time of the silver salt solution in the reaction vessel was 157 seconds. The temperature of the raw material solution and the silver salt solution was 20° C. Subsequently, while adding dropwise the aqueous phase (silver salt solution containing PUFA ethyl ester) collected from the first column to the second column (extraction vessel, argon gas was blown and air was purged) filled with an organic solvent at 60° C. through the supply port in the column at a flow rate of 11 g/min, an organic solvent at 60° C. was injected from the lower part of the column. With this, the aqueous phase was contacted with the organic solvent to extract a PUFA ethyl ester in the aqueous phase into the organic phase. Concurrently with the dropwise addition of the aqueous phase and the injection of the organic solvent, while collecting the silver salt solution accumulated in the lower part of the second column at a flow rate of 10 g/min, the organic phase into which the PUFA ethyl ester has been extracted from the upper part of the column. The distance between the nozzle tip of the second column supply port and the top surface of the aqueous phase was maintained at 13 cm. The linear velocity of the aqueous phase flowing in the extraction vessel was 0.1 cm/sec, and the retention time of the silver salt solution in the reaction vessel was 157 seconds. The organic phase (organic solvent containing a PUFA ethyl ester) collected from the second column was concentrated to obtain a PUFA ethyl ester-containing composition. A part of the aqueous phase (silver salt solution) collected from the second column subjected to measurement for the free fatty acid content, and the rest was re-used. A series of steps as mentioned above was defined as one process, and the process was repeated. The raw material solution in the first column was replaced with a fresh one for each process.

Figure 3:
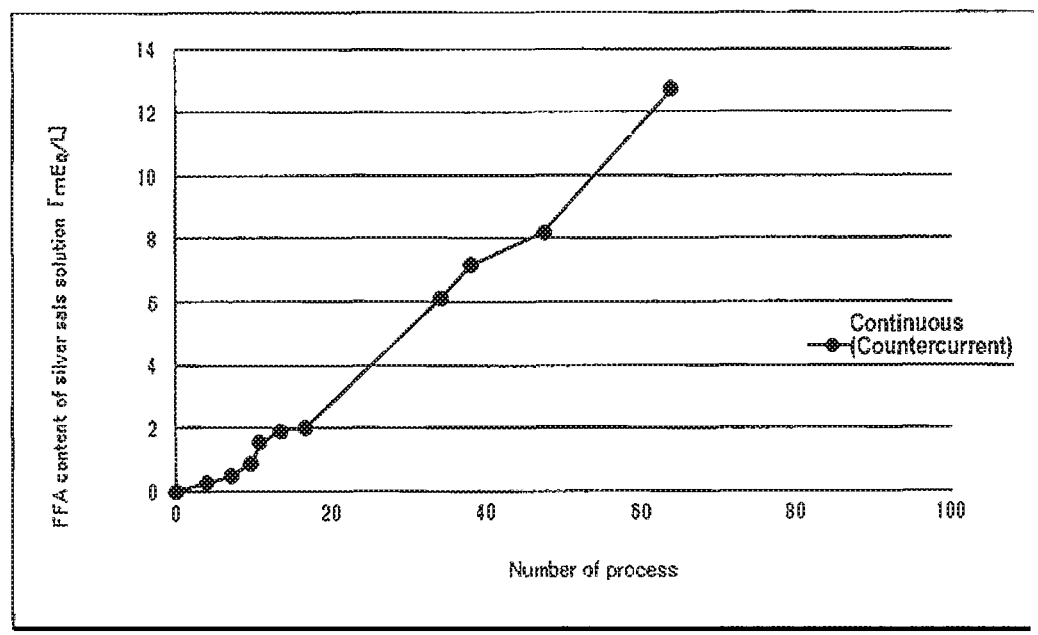
FIG. 3 illustrates a change over time in a free fatty acid content with repeated use of the silver salt solution in a continuous mode using a countercurrent flow.

The free fatty acid (FFA) content in the silver salt solution after use was measured according to Reference Example 2 after several processes. The temporal change of the free fatty acid (FFA) content with repeated use (number of processes) of the silver salt solution are illustrated in FIG. 3.

The invention claimed is:

1. A method for producing a polyunsaturated fatty acid-containing composition, the method comprising:

supplying a raw material solution comprising an alkyl ester of polyunsaturated fatty acid and an aqueous solution comprising a silver salt to a flow channel mixer to contact the raw material solution with the aqueous solution; and collecting the aqueous solution comprising the silver salt which has been contacted with the raw material solution, wherein the supplying of the aqueous solution comprising the silver salt to the flow channel mixer and the collecting of the aqueous solution comprising the silver salt which has been contacted with the raw material solution are performed concurrently with each other.

2. The method according to claim 1, further comprising:

supplying the aqueous solution comprising the silver salt which has been collected from the flow channel mixer and an organic solvent to an extraction vessel to contact the organic solvent with the aqueous solution comprising the silver salt which has been collected from the flow channel mixer; and collecting the organic solvent which has been contacted with the aqueous solution comprising the silver salt which has been collected from the flow channel mixer, wherein the supplying of the aqueous solution comprising the silver salt which has been collected from the flow channel mixer to the extraction vessel and the collecting of the organic solvent which has been contacted with the aqueous solution comprising the silver salt which has been collected from the flow channel mixer are performed concurrently with each other.

3. The method according to claim 1, wherein the collecting of the aqueous solution comprising the silver salt which has been contacted with the raw material solution comprises collecting a mixed solution of the aqueous solution comprising the silver salt and the raw material solution from the flow channel mixer and then fractionating the aqueous solution comprising the silver salt from the collected mixed solution.

4. The method according to claim 2, wherein the collecting of the organic solvent which has been contacted with the aqueous solution comprising the silver salt comprises collecting a mixed solution of the aqueous solution comprising the silver salt and the organic solvent from the extraction vessel and then fractionating the organic solvent from the collected mixed solution.

5. The method according to claim 1, further comprising:
supplying the raw material solution which has been collected from the flow channel mixer to a flow channel mixer again.

6. The method according to claim 1, wherein the supplying of the aqueous solution comprising the silver salt to the flow channel mixer, the contacting of the aqueous solution comprising the silver salt with the raw material solution, and the collecting of the aqueous solution comprising the silver salt which has been contacted with the raw material solution from the flow channel mixer are performed under hypoxic conditions.

7. The method according to claim 1, wherein a linear velocity of the aqueous solution comprising the silver salt in the flow channel mixer is 0.5 cm/sec or more.

8. The method according to claim 1, wherein the flow channel mixer has an inner diameter of 0.1 to 100 cm and a length of 0.05 to 10 m.

9. The method according to claim 1, wherein a retention time of the aqueous solution comprising the silver salt in the flow channel mixer is from 0.02 to 300 seconds.

10. The method according to claim 1, wherein a temperature of the aqueous solution comprising the silver salt upon contact with the raw material solution is from 5° C. to 30° C.

11. The method according to claim 2, wherein the extraction vessel is a flow channel mixer.

12. The method according to claim 11, wherein a linear velocity of the aqueous solution comprising the silver salt in the extraction vessel is 0.5 cm/sec or more.

13. The method according to claim 11, wherein the extraction vessel has an inner diameter of 0.1 to 100 cm and a length of 0.05 to 10 m.

14. The method according to claim 11, wherein a retention time of the aqueous solution comprising the silver salt in the extraction vessel is from 0.02 to 300 seconds.

15. The method according to claim 2, wherein a temperature of the aqueous solution comprising the silver salt upon contact with the organic solvent is from 30° C. to 80° C.

16. The method according to claim 1, wherein the raw material solution comprising an alkyl ester of polyunsaturated fatty acid has such an oxidation index that a POV is 10 or less, or AV is 0.3 or less.

17. The method according to claim 1, wherein the polyunsaturated fatty acid comprises eicosapentaenoic acid or docosahexaenoic acid.

18. The method according to claim 2, further comprising:
supplying the raw material solution which has been collected from the flow channel mixer to a flow channel mixer again.

19. The method according to claim 2, wherein the supplying of the aqueous solution comprising the silver salt to the flow channel mixer, the contacting of the aqueous solution comprising the silver salt with the raw material solution, and the collecting of the aqueous solution comprising the silver salt which has been contacted with the raw material solution from the flow channel mixer are performed under hypoxic conditions.

20. The method according to claim 2, wherein a linear velocity of the aqueous solution comprising the silver salt in the flow channel mixer is 0.5 cm/sec or more.

21. The method according to claim 2, wherein the flow channel mixer has an inner diameter of 0.1 to 100 cm and a length of 0.05 to 10 m.

22. The method according to claim 2, wherein a retention time of the aqueous solution comprising the silver salt in the flow channel mixer is from 0.02 to 300 seconds.

23. The method according to claim 2, wherein a temperature of the aqueous solution comprising the silver salt upon contact with the raw material solution is from 5° C. to 30° C.

24. The method according to claim 2, wherein the raw material solution comprising an alkyl ester of polyunsaturated fatty acid has such an oxidation index that a POV is 10 or less, or AV is 0.3 or less.

\* \* \* \* \*